United States Patent [19]

Rowland

[11] Patent Number: 4,627,860

[45] Date of Patent: Dec. 9, 1986

[54] OXYGEN CONCENTRATOR AND TEST APPARATUS

[75] Inventor: Robert O. Rowland, Hemet, Calif.

[73] Assignee: Hudson Oxygen Therapy Sales Company, Temecula, Calif.

[21] Appl. No.: 713,339

[22] Filed: Mar. 18, 1985

Related U.S. Application Data

[63] Continuation-in-part of Ser. No. 634,595, Jul. 26, 1984, Pat. No. 4,561,287, which is a continuation-in-part of Ser. No. 396,705, Jul. 9, 1982, Pat. No. 4,516,424.

[51] Int. Cl.⁴ ............................................. B01D 53/04
[52] U.S. Cl. ...................................... 55/162; 55/163; 55/179; 55/270; 55/274; 55/387; 128/204.22; 128/205.12
[58] Field of Search ................... 55/18, 21, 25, 26, 58, 55/68, 161–163, 179, 270, 274, 387, 389; 128/202.26, 204.21, 204.22, 205.12, 205.28, 906

[56] References Cited

U.S. PATENT DOCUMENTS

| | | | |
|---|---|---|---|
| 2,944,627 | 7/1960 | Skarstrom | 55/58 X |
| 3,142,547 | 7/1964 | Marsh et al. | 55/58 X |
| 3,280,536 | 10/1966 | Berlin | 55/58 |
| 3,566,370 | 2/1971 | Worthington, Jr. et al. | 128/906 X |
| 3,715,866 | 2/1973 | Chatlos et al. | 55/270 X |
| 3,880,616 | 4/1975 | Myers et al. | 55/179 X |
| 3,898,047 | 8/1975 | Cramer | 128/202.26 X |
| 3,922,149 | 11/1975 | Ruder et al. | 55/21 |
| 4,068,096 | 1/1978 | Rattenborg et al. | 179/2 A |
| 4,197,095 | 4/1980 | White, Jr. et al. | 55/21 X |
| 4,222,750 | 9/1980 | Gauthier et al. | 55/58 |
| 4,247,311 | 1/1981 | Seibert et al. | 55/162 |
| 4,262,248 | 4/1981 | Vincelli et al. | 324/73 R |
| 4,329,643 | 5/1982 | Neumann et al. | 324/158 F |
| 4,331,455 | 5/1982 | Sato | 55/21 |
| 4,336,590 | 6/1982 | Jacq et al. | 128/204.22 X |
| 4,349,357 | 9/1982 | Russell | 55/21 |
| 4,404,005 | 9/1983 | Hamlin et al. | 55/163 |
| 4,428,372 | 1/1984 | Beysel et al. | 128/202.26 |
| 4,449,990 | 5/1984 | Tedford, Jr. | 55/58 X |
| 4,545,790 | 10/1985 | Miller et al. | 55/179 X |

FOREIGN PATENT DOCUMENTS 2003742  3/1979  United Kingdom .
2029257  3/1980  United Kingdom .

Primary Examiner—Robert Spitzer
Attorney, Agent, or Firm—Seiler, Quirk & Tratos

[57] ABSTRACT

An improved oxygen concentrator assembly includes a microprocessor and cooperating means for monitoring or sensing functions and performance of various components of the concentrator. A test apparatus having means for selecting any of the functions monitored by the microprocessor is connected to the concentrator and displays the selected monitored functions for diagnosing performance levels and component problems or failures.

26 Claims, 5 Drawing Figures

OXYGEN CONCENTRATOR AND TEST APPARATUS

REFERENCE TO OTHER APPLICATIONS

This application is a continuation-in-part of my prior co-pending application Ser. No. 634,595, filed July 26, 1984, now U.S. Pat. No. 4,561,287 which is a continuation-in-part of Ser. No. 396,705, filed July 9, 1982, now U.S. Pat. No. 4,516,424.

BACKGROUND OF THE INVENTION

Oxygen concentrators have become used extensively for supplying oxygen-enriched gas to respiratory patients, particularly those requiring relatively high oxygen concentrations in a breathable gaseous mixture over extended periods of time. Because oxygen concentrators deliver a breathable gas of between about 80-96% oxygen from atmospheric air, thereby eliminating the requirement of bottled gas, oxygen cylinders, and the like, they have found substantial appeal especially in the home care field.

In my aforesaid prior co-pending application Ser. No. 396,705, there is described an improved oxygen concentrator which monitors the oxygen concentration of the product gas and rate of product gas withdrawal, and makes necessary adjustments in the timing cycle to achieve necessary minimum oxygen concentrations. In the concentrator of my prior application Ser. No. 634,595, the apparatus automatically adjusts itself for minimizing power consumption.

Often there are a number of factors which may need to be considered by a technician in evaluating the performance of the concentrator, especially in anticipating malfunctions or sieve bed deterioration in performing preventative maintenance. In addition, because of the cost of making service or maintenance calls on concentrators installed in homes, particularly in rural or remote areas from the service center or dealership, remote performance monitoring and diagnosis of the apparatus is of particular interest.

SUMMARY OF THE INVENTION

In the improved oxygen concentrator of the invention a plurality of components and functions of the concentrator assembly are monitored by the controller to which a portable testing apparatus may be connected for selectively monitoring the different diagnostic functions. The test apparatus may also be used at a remote location and cooperating with modems, receive transmitted signals for monitoring such diagnostics.

DETAILED DESCRIPTION OF THE INVENTION

Figure 1:
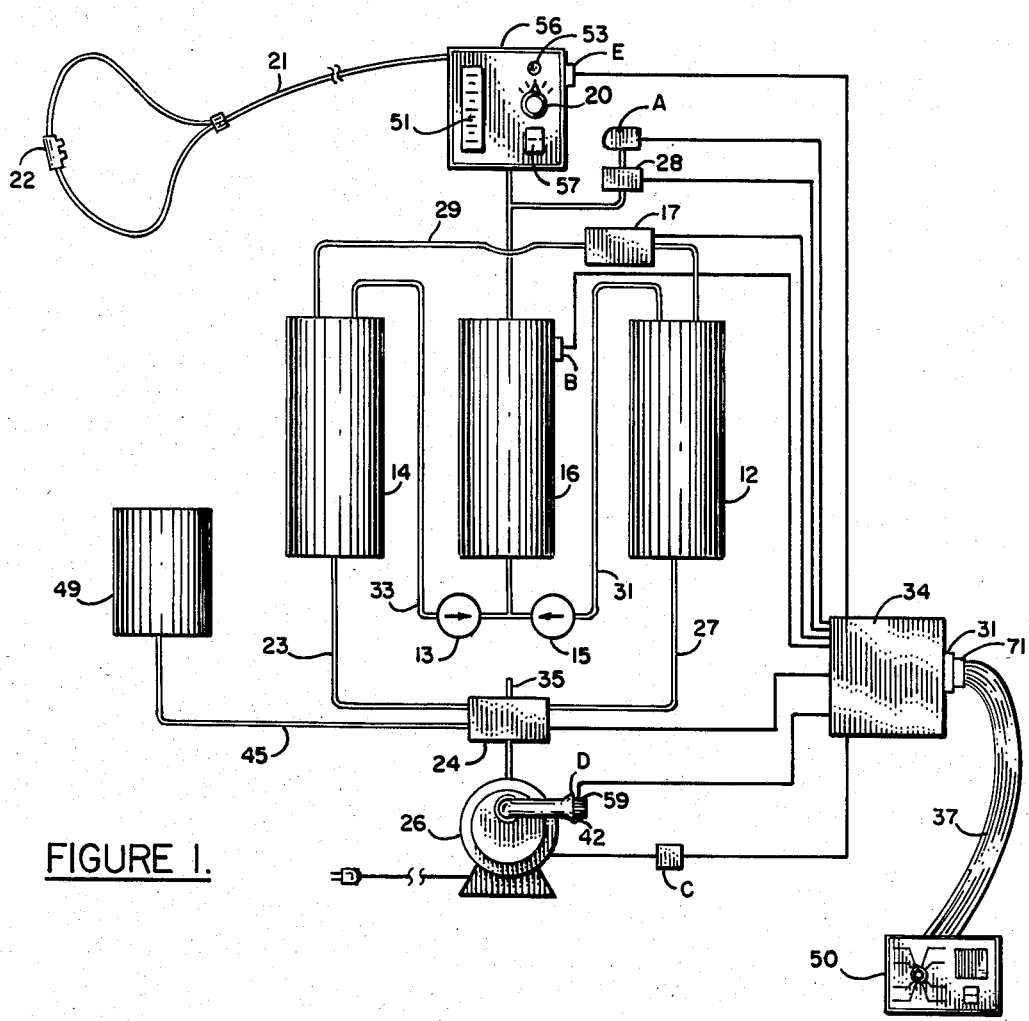
FIG. 1 illustrates schematically an improved oxygen concentrator apparatus including a microcomputer for monitoring a number of different concentrator functions and the test apparatus.

In FIG. 1, there is illustrated generally the oxygen concentrator of the invention. The apparatus includes a compressor 26 which charges atmospheric air alternately into cannisters 12 and 14 containing molecular sieve material for selectively adsorbing nitrogen from the gas. Between the cannisters is reservoir tank 16 for holding the oxygen-enriched product gas recovered from the sieve beds. Suitable conduits, pipes and valves direct gas between the cannisters and the reservoir.

Generally, in operation, when power switch 57 is activated atmospheric air is drawn into compressor 26 via inlet pipe 42 and is forced via pipe 11 to four-way valve 24 where it is alternately directed to sieve bed cannisters 12 and 14. The timing cycle for operating valve 24 is regulated by controller 34 which includes timing means for switching the valve. Atmospheric air is directed under pressure to cannister 12 via conduit 27, and nitrogen is selectively adsorbed from the air as pressure in the cannister is increased. The oxygen-enriched product gas from cannister 12 is then directed via conduit 31 through one-way valve 15 into reservoir 16. At a preselected time interval, valve 24 switches the gas flow and directs air to cannister 14 via conduit 23 with the oxygen-enriched product gas passing into reservoir 16 via pipe 33 and one-way valve 13 as previously described. After a sieve bed has gone through a pressurized nitrogen adsorption cycle, pressure is relieved causing release of the adsorbed nitrogen, which is then vented to atmosphere by valve 24 via outlet pipe 35. Thus, the valve simply cycles to pressurize one cannister while the other cannister is being vented, and this cycle continues so long as gaseous product is demanded by use as it is withdrawn from reservoir 16.

The apparatus includes a two-way valve 17 which is open temporarily during a purge cycle whereby oxygen-enriched product gas from one cannister is directed to the other via pipe 29 to remove residual nitrogen. The operation of valve 17 including its timing sequence is regulated by a second timing function of controller 34. Near the end of the period when product gas is being directed to the reservoir from one cannister and nitrogen is simultaneously vented from the other, valve 17 opens for a short time to allow a final portion of the oxygen-enriched product gas to pass into the venting cannister and purge any residual nitrogen. Thus, each cannister alternately adsorbs nitrogen from atmospheric air, the oxygen-enriched gas is directed into reservoir 16, pressure is relieved in the cannister to vent adsorbed nitrogen to atmosphere, and residual nitrogen in the cannister is purged by the flow of oxygen-enriched gas from the other cannister. The cannister is then ready for another charge of atmospheric air to again begin the nitrogen adsorption cycle. Oxygen-enriched product gas is withdrawn from reservoir 16 via valve 20 through flow meter 51 where it is dispensed to a patient via tube 21 and nasal cannula 22, oxygen mask or other delivery means. The general functioning of oxygen concentrators utilizing two adsorption cannisters containing molecular sieve material is well known in the art, and described, for example, in U.S. Pat. Nos. 2,944,627, 3,142,547, 3,280,536, and 3,898,047. Specific portions of these patents for further explaining the operation of oxygen concentrators are incorporated herein by reference.

FIG. 1 illustrates a preferred embodiment of the oxygen concentrator apparatus, incorporating in addition to the previously described components, a surge tank 49 connected to valve 24 by conduit 45. The purpose of the surge tank is to receive atmospheric air charged by compressor 26 during the time when neither of the sieve bed cannisters 12 and 14 are being pressurized. In this embodiment valve 24 switches from a first position in which cannister 12 is pressurized and cannister 14 is vented and purged, a second position when cannister 14 is pressurized and cannister 12 is vented and purged, and a dead time or neutral position in which the compressor directs atmospheric air to surge tank 49 when neither cannister is pressurized. This valve functioning and the provision of the surge tank will prevent the compressor from working against a dead-head time during which the valve is closed and passing between the first and second positions. Thus, when the valve is in the intermediate position as it switches between the first and second positions the compressor will charge the surge tank via pipe 45. Moreover, because the surge tank is pressurized, when the valve is in either the first or second position, pressurized air will pass from the surge tank through the open valve to assist in pressurizing the sieve beds. The length of time valve 24 is in the neutral position is also controlled by controller 34. Thus, the controller also functions as previously described to regulate the length of time the valve remains in the first and second positions as well as the intermediate or neutral position switching time (dead-time) between the first and second positions for charging the surge tank.

In the improved apparatus of the invention, the concentrator includes a controller and cooperating components for not only controlling the operation of the apparatus as previously described but which monitors the functioning or output of various components. Moreover, a test apparatus is provided, which, when electrically connected to the controller, will allow an operator to select different monitored functions and output of the concentrator and visually display the monitored results. An important function of the apparatus of the invention is in monitoring the concentration of oxygen in the product gas produced and delivered by the oxygen concentrator. For this purpose, controller 34 monitors oxygen sensor A which senses the oxygen concentration in product gas directed from reservoir 16. Where the oxygen sensor is of the fuel cell or polaragraphic type, the life of which is sensitive to the concentration of oxygen gas monitored, the apparatus preferably includes valve 28 the functioning of which is regulated by the controller for selectively and alternately directing oxygen-enriched product gas and atmospheric air, respectively, to the sensor. Moreover, such alternate gas sensing is also advantageous because the sensor may be calibrated with atmospheric air. Such a feature is further specifically disclosed in my aforesaid prior applications, the description of which is incorporated herein by reference. However, other types of sensors may be used including ultrasonic devices which may not require such calibration or which do not deteriorate proportionately with use.

Another important monitoring function of the apparatus is to determine the product gas withdrawal rate from reservoir 16. This is preferably accomplished by utilizing a pressure transducer B electrically connected to the controller. The microprocessor of the controller determines the flow rate of product gas from reservoir 16 from changes in the pressure sensings which may be carried out at preselected intervals by the controller. Such a transducer means for determining product gas flow is more specifically described in my aforesaid prior applications, the description of which is incorporated herein by reference. Other means for measuring product gas withdrawal rates and means for sensing such rates may also be used. For example, flow rates across a fixed orifice may be measured by mounting transducers measuring pressure drop across the orifice.

In the preferred apparatus, another desired monitoring function is sensing the peak pressure in each of the plurality of molecular sieve beds. This is accomplished by sensing the pressure in reservoir 16 via pressure transducers at the time of maximum pressurization for each of the sieve beds. Times and intervals for making such readings are provided as functions of the controller which may also include memory means for holding the most recent peak sieve bed pressure.

Another desired monitoring function of the apparatus is for sensing the line voltage supplied to operate the compressor. This may be accomplished by monitoring a transformer C connected to the compressor power cord which drops and transforms the line voltage to a DC current to be read by the microprocessor in direct proportion to the line voltage. Another desired feature includes means for displaying the time for charging each of the sieve beds, or cycle time. This is accomplished internally within the controller which itself controls the timing cycle for operating valve 24.

Other optional features include means for monitoring the amount of restriction at the concentrator inlet filter 59. For this purpose, a vacuum switch D on the compressor side of the filter may be monitored which senses the pressure drop across the inlet filter thereby indicating the degree of restriction as atmospheric air is drawn into the compressor inlet 42. As the pressure drop across the filter increases, plugging of the filter dictates replacement or cleaning.

Another desirable monitoring device includes means for sensing the voltage of a battery used to power the concentrator alarm indicators. Such a device E is shown adjacent concentrator display panel 56 where the battery, commonly a 9 volt battery, may be conveniently located. The battery operates visual alarm indicator or light 53 on the panel 56 or an audible alarm (not shown). Thus, such a sensing device simply monitors the battery voltage thereby giving notice to the test apparatus operator of a low battery condition.

The oxygen sensor output may also be monitored by measuring the electrical output of the sampling system sensor, for example, in microamps and as a function of the sensed oxygen concentration as previously described. Such a feature is used to diagnosis sensor problems. The test apparatus may also display the cycle time for pressurizing the sieve beds, as well as the surge time, or the time in which four-way valve 24 is in a neutral position for charging surge tank 49. Since the timing cycle of the four-way valve 24 is controlled by controller 34, the test apparatus simply reads and displays the cycle time and purge time, in seconds, from the controller.

Another monitoring function includes means for sensing the average of sieve bed peak pressures which information may be used to calibrate the concentrator pressure transducer. A service register function may be used to indicate the problem which has caused the alarm or service indicator on the concentrator display panel to light and/or sound. Such prompters preferably include low and high sieve pressures, low concentration and circuit board problems. A history register may be used to display codes or diagnostic prompters which relate to the function of the concentrator over a period of time. Any desired prompter numerals may be used for describing any selected diagnostic problems and may be displayed in sequence, one at a time, in the order of most recent occurrence, which may be useful for assisting in trouble shooting and repairing the apparatus.

Figure 3:
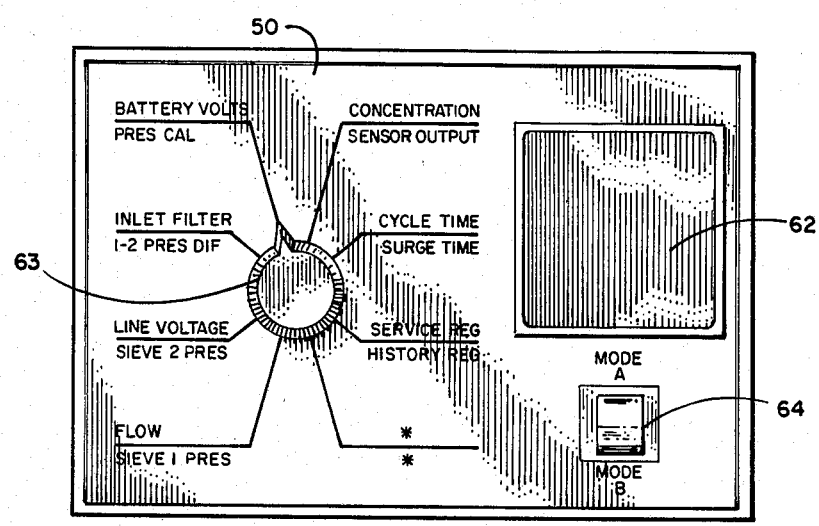
FIG. 3 is a front view of the test apparatus illustrating the diagnostic functions to be selectively monitored.

In FIG. 3 there is illustrated a sample of the face of a test apparatus 50 which includes knob 63 which may be rotated to select the desired test function. Mode switch 64 also cooperates with dial 63 whereby either of two diagnostic procedures may be selected at a single dial location. Screen 62 will display the monitor test results. Referring again to FIG. 1, cable 37 and socket 31 extending from test apparatus 50 may be plugged in to the appropriate receptacle of the concentrator so that the test box is electrically connected to controller 34 which includes the microcomputer which monitors the various functions of the concentrator. In order to test the concentrator functions, the concentrator must be in operation, preferably for at least a few minutes. Then, the test apparatus is simply plugged in and the operator selects the desired tests and observes the visually displayed results.

Figure 2:
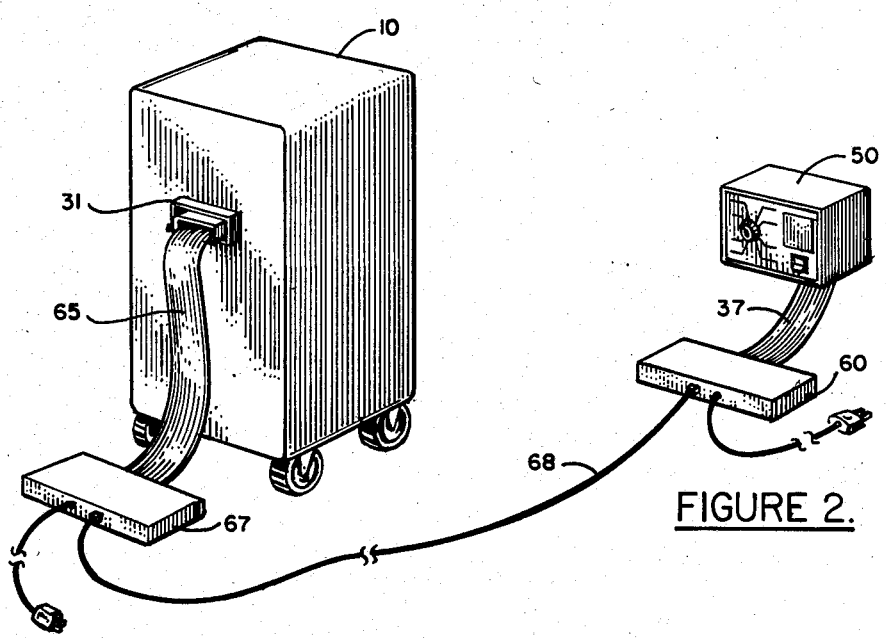
FIG. 2 illustrates a remote test apparatus for the concentrator.

A further preferred embodiment of the apparatus is shown in FIG. 2 illustrating the concept of remote communication between test apparatus 50 and oxygen concentrator 10 utilizing telephone or similar communication line 68. In such an embodiment, modems which convert data signals from the concentrator to signals which may be transmitted or carried over telephone lines are used, a first modem 60 at the remote location and connected to test apparatus 50 via cable 37, and second modem 67 connected to concentrator 10 via cable 65. Such remote testing may be advantageous in a number of ways. Particularly, where the concentrator is located at some distance away from the service center, such remote diagnostics will be highly useful in either trouble shooting concentrator problems which have occurred and the seriousness and/or cause of which may be determined at the remote service center. Or, such remote diagnostics are particularly advantageous in preventative maintenance checks without making a service call. For example, where a service center has a test apparatus 50 and a modem 60, and the concentrator is connected to a modem 67, a service man may "dial-up" the concentrator via the modems and telephone line 68 and carry out the diagnostic procedure utilizing the test apparatus 50. Of course, such a diagnosis will determine any malfunctions as well as performance levels of the concentrator. Utilizing such a system, the service center may selectively and periodically check any concentrators which are provided with the appropriate modem communication means. Such an apparatus will present substantial advantages in time and expense in maintaining concentrators in working condition without unnecessary maintenance and service calls.

An alternative function may be achieved by providing the concentrator with microprocessor means for signaling modem 67 to "dial-up" the remote test apparatus when a problem or malfunction occurs. For example, when oxygen concentration levels sensed by the controller are below minimum requirements over a preselected series of readings, the controller will signal the modem to alert the service center, for example, by displaying some preselected code or number on the test apparatus which will identify the location of the concentrator. Thus, the concentrator itself may be programmed to initiate the testing procedure to point out the malfunction.

Figure 4:
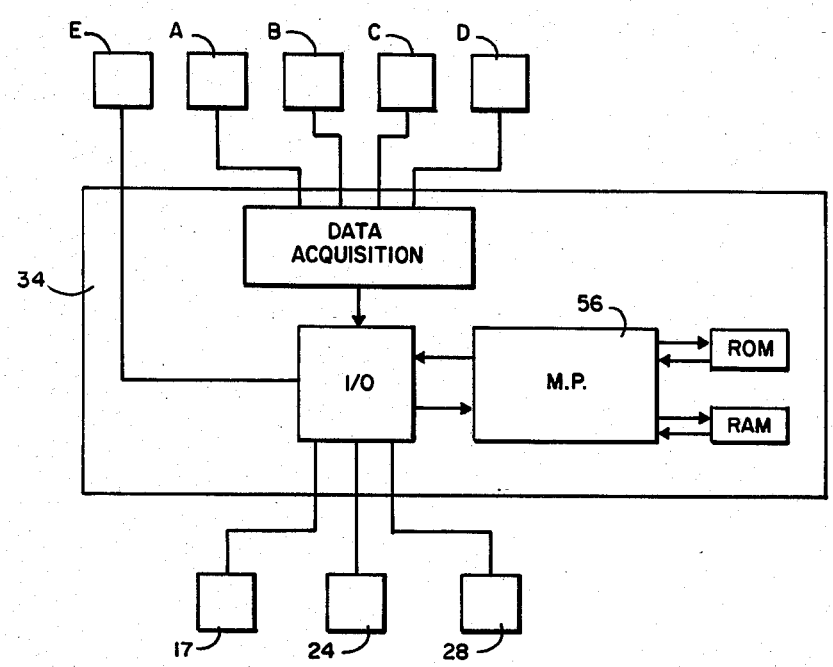
FIG. 4 schematically illustrates the controller and diagnostics monitoring feature of the concentrator.

FIG. 4 illustrates generally the design and function of controller 34. A ROM memory circuit in the microprocessor 56 may be provided with minimum oxygen concentrations or charging time requirements for different product gas flow rates as well as any other desired memory functions including, for example, location or telephone code of the concentrator, etc. The various sensors A–D, also illustrated in FIG. 1 direct signals to a data acquisition module which provides an analog-digital conversion function which is then directed to input/output module for operating valves 17, 24 and 28 as directed by the microprocessor. The battery sensing monitor means E provides a digital signal so is directly connected to the I/O module. A RAM memory circuit is useful for temporarily storing sensor readings to be directed to the test apparatus, and is normally a component of the microprocessor.

Figure 5:
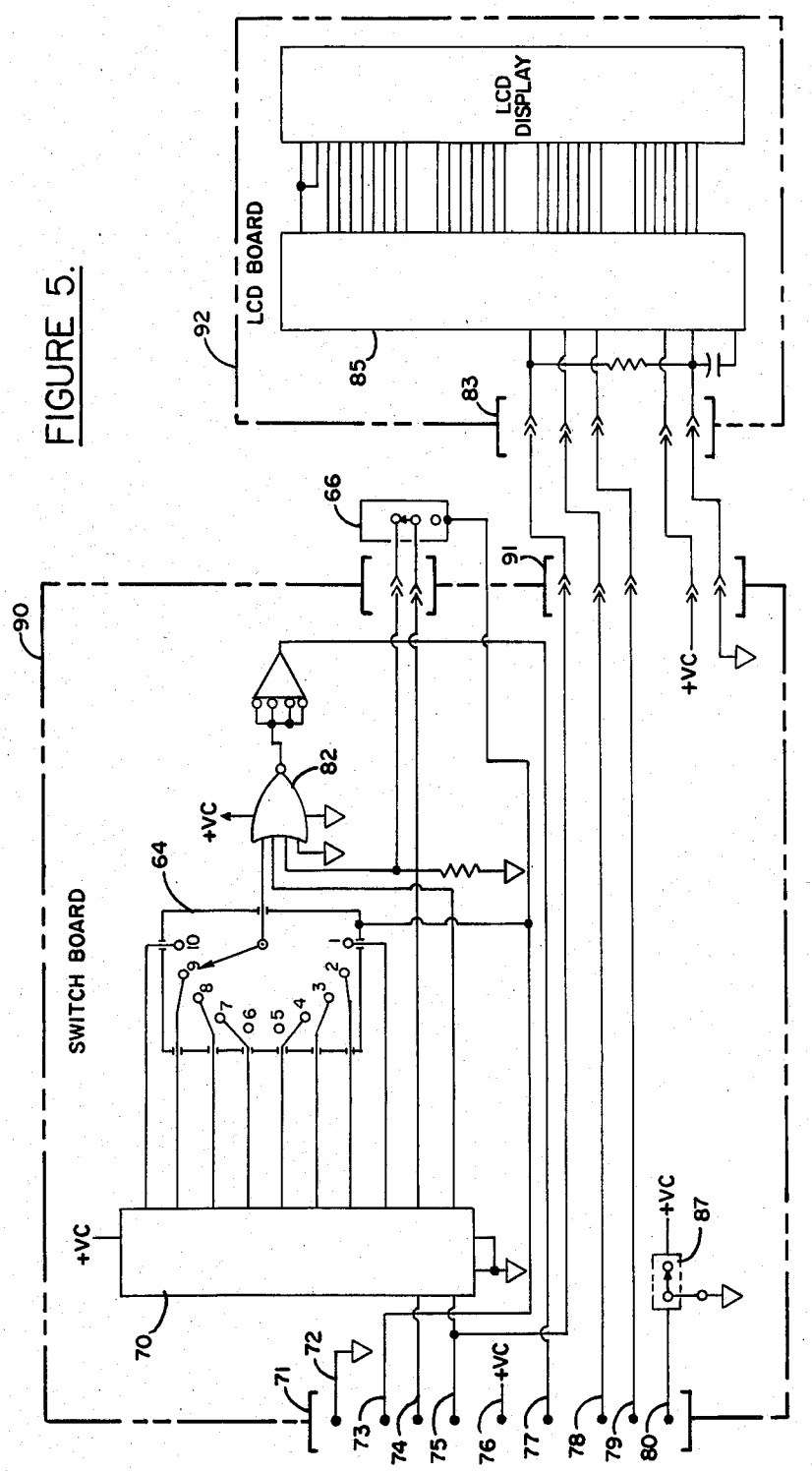
FIG. 5 is a circuit diagram of the test apparatus.

FIG. 5 shows the test apparatus schematic circuit diagram. A receptacle or socket 71 incorporates a number of pins connected to lines for operating the test apparatus. The socket may be attached to an external cable 37 for being connected to the concentrator as shown in FIG. 1. Internal sockets 91 and 83 connect lines between the switch board 90 and LCD board 92. Incoming lines from socket 71 into the switch board include ground 72, electrostatic discharge ground 73, reset pulse line 74, clock pulse line 75, input power line (+5 v) 76 data output line 77, data display line 78, display load pulse line 79 and device select line 80. Other components of the switch board include a stepping counter 70, ten position rotating switch 64, rotated by turning knob 63 on the front panel (FIG. 3), OR gate 82, and a jumper switch 87. In the LCD board 92, integrated circuit 85 contains a 32 bit shift register, a display register and the LCD driver. Mode switch 66 is operated by mode switch 64 on the panel of the test apparatus shown in FIG. 3.

In operation, to read the test function selected by the rotating switch 64, the microprocessor of the oxygen concentrator first sends a reset pulse (line 74) to counter 70 to clear all of the outputs to zero. It then sends a series of ten clock pulses (line 75) to the counter and reads the output from each of the switch positions of switch 64 after each pulse. A pulse is then sent to mode switch 66 and checks its output to determine its position. To update the display on the test apparatus, the concentrator microprocessor sends a data string of four groups of eight clock pulses (line 78) to integrated circuit 85 to turn on the proper display segments. After the last group of eight pulses, a load pulse is sent on line 79 which transfers the data from the shift register to the display register. The data in the display register is then converted to an AC signal and sent to the LCD display 84.

The oxygen concentrator may also include means for maintaining selected oxygen concentrations in the product gas by changing the times for charging sieve beds 12 and 14. To achieve such a function, controller 34 will include means for comparing the oxygen concentration monitored by sensor 36 with a preselected reference concentration, and operate valves 24 and 17 to achieve necessary product gas concentration. Such a function and means therefore are disclosed in my aforesaid prior applications, and is incorporated herein by reference. Still another preferred feature of the oxygen concentrator of the invention is in minimizing the power requirements for operating the apparatus, also disclosed in my aforesaid prior application Ser. No. 634,595 and is incorporated herein by reference.

I claim:

1. In an oxygen concentrator comprising
    a plurality of molecular sieve beds for alternately receiving atmospheric air for selectively adsorbing nitrogen therefrom to increase the oxygen concentration of an oxygen enriched product gas recovered therefrom,
    a reservoir for receiving said product gas from said sieve beds and flow control means for selecting the withdrawal rate of said product gas from said reservoir,
    a compressor including means for providing line voltage for operating said compressor, and
    a valve cooperating with said compressor for alternately charging said sieve beds with atmospheric air and timing means for switching said valve to alternately charge said sieve beds according to a timing cycle, the improvement comprising
    (a) flow rate sensing means independent of said flow control means for sensing the rate of withdrawal of product gas from said reservoir and for communicating the sensed rate of withdrawal of said product gas to a modem,
    (b) oxygen sensing means for sensing the oxygen concentration in said oxygen enriched product gas and for communicating the sensed oxygen concentration in said product gas to a modem,
    (c) a modem for receiving quantitative signals communicated from said flow rate sensing means and said oxygen sensing means and for transmitting said signals to a remote test apparatus, and
    (d) a remote test apparatus in telephonic communication with said modem for receiving transmitted signals from said modem and having means for displaying the flow rate and oxygen concentration of said product gas.

2. The concentrator of claim 1 wherein said flow rate sensor comprises a pressure transducer in said reservoir for measuring product gas pressure therein.

3. The concentrator of claim 2 including a microprocessor cooperating with said pressure transducer and having means for determining the rate of flow of product gas from said reservoir in response to pressure sensings therein.

4. The concentrator of claim 3 wherein said test apparatus includes visual display means for displaying the product gas flow rate and the oxygen concentration, and means for selecting the test to be displayed.

5. The concentrator of claim 1 wherein said remote test apparatus includes means for selectively signaling said modem to transmit said signals from said concentrator.

6. The concentrator of claim 1 including a microprocessor having means for receiving the sensed rate of product gas withdrawal from said flow rate sensing means and for receiving the oxygen concentration in said product gas from said oxygen sensing means and having memory means provided with minimum selected product gas oxygen concentrations at different product gas withdrawal rates, respectively, means for comparing the sensed product gas oxygen concentrations with the minimum selected concentration at the sensed withdrawal rate, and means for signaling said modem to transmit said signals to said remote test apparatus when said sensed oxygen concentration falls below said minimum selected concentration.

7. In an oxygen concentrator comprising
    a plurality of molecular sieve beds for alternately receiving atmospheric air for selectively adsorbing nitrogen therefrom to increase the oxygen concentration of a product gas recovered therefrom,
    a reservoir for receiving said product gas from said sieve beds and flow control means for selecting the withdrawal rate of said product gas from said reservoir,
    a compressor including means for providing line voltage for operating said compressor, and
    a valve cooperating with said compressor for alternately charging said sieve beds with atmospheric air and timing means for switching said valve to alternately charge said sieve beds according to a timing cycle, the improvement comprising:
    (a) flow rate sensing means independent of said flow control means for sensing the flow rate of product gas from said reservoir and means for communicating the sensed flow rate to a microprocessor,
    (b) an oxygen sensor for measuring the oxygen concentration of said product gas and means for communicating the sensed oxygen concentration to a microprocessor,
    (c) a microprocessor cooperating with said flow rate sensing means and said oxygen sensor for receiving quantitative signals therefrom and memory means for storing the last determined product gas flow rate and sensed oxygen concentration, and
    (d) a testing apparatus removably connected with said microprocessor having digital display means for displaying data received from said microprocessor, and means for selecting test data from said microprocessor to be displayed.

8. The oxygen concentrator of claim 7 wherein said flow rate sensing means comprises a pressure transducer in said reservoir for measuring product gas pressure therein, and wherein said microprocessor includes means for determining product gas flow rate from said reservoir based on the reservoir pressure sensings.

9. The concentrator of claim 8 wherein said microprocessor includes memory means provided with minimum selected product gas oxygen concentrations at different product gas withdrawal rates, respectively, means for comparing the sensed product gas oxygen concentration with the minimum selected concentration at the sensed withdrawal rate, and alarm means cooperating with said microprocessor for indicating when said sensed oxygen concentration falls below said minimum selected concentration.

10. The oxygen concentrator of claim 9 including modem means between said microprocessor and said testing apparatus and in communication therewith for receiving quantitative product gas flow rate and oxygen concentration signals from said microprocessor and for transmitting said signals to said test apparatus.

11. The oxygen concentrator of claim 10 wherein said modem means comprises a first modem connected to said microprocessor and a second remote modem connected to said test apparatus at a remote location, and wherein said modems are in telephonic communication.

12. The concentrator of claim 11 wherein said microprocessor includes means for signaling said first modem to transmit said signals to said test apparatus when said sensed oxygen concentration falls below said minimum selected concentration.

13. The oxygen concentrator of claim 7 including at least one of the following components:
    (i) first means for sensing peak pressure in each of said plurality of molecular sieve beds, and
    (ii) second means for sensing the line voltage supplied to operate said compressor.

14. The oxygen concentrator of claim 7 wherein said testing apparatus includes means for selecting display of the time required to charge each of said sieve beds.

15. The oxygen concentrator of claim 14 including a surge tank communicating with said compressor and being charged with air from said compressor when said valve is in a neutral position, and wherein said testing apparatus includes means for selecting display of the time in which said valve is in said neutral position.

16. In an oxygen concentrator for increasing the oxygen concentration of a gaseous mixture comprising a valve having a first position for charging atmospheric air under pressure from a compressor into a molecular sieve bed and selectively adsorbing nitrogen therefrom to produce an oxygen enriched gaseous product and a second position in which desorbed nitrogen is released from said sieve bed, a reservoir for receiving said gaseous product from said sieve bed and flow control means for selecting the withdrawal rate of said product gas from said reservoir, the improvement comprising:
    (a) flow rate sensing means independent of said flow control means for sensing the flow rate of gaseous product withdrawn from said reservoir and means for communicating the sensed flow rate to a microprocessor,
    (b) oxygen sensor for sensing the oxygen concentration of said gaseous product and means for communicating the measured oxygen concentration to a microprocessor,
    (c) a microprocessor cooperating with said flow rate sensing means and said oxygen sensor for receiving quantitative signals therefrom and memory means for storing the last determined gaseous product flow rate and sensed oxygen concentration, and
    (d) a testing apparatus removably connected with said microprocessor having selective digital display means for displaying the gaseous product flow rate and sensed oxygen concentration received from said microprocessor.

17. The concentrator of claim 16 wherein said flow rate sensor comprises a pressure transducer in said reservoir for measuring gaseous product pressure therein.

18. The oxygen concentrator of claim 16 wherein said flow rate sensing means comprises a pressure transducer in said reservoir for measuring product gas pressure therein, and wherein said microprocessor includes means for determining gaseous flow rate from said reservoir based on the reservoir pressure sensings.

19. The concentrator of claim 18 wherein said microprocessor includes memory means provided with minimum selected gaseous product oxygen concentrations at different withdrawal rates, respectively, means for comparing the sensed gaseous product oxygen concentration with the minimum selected concentration at the sensed withdrawal rate, and alarm means cooperating with said microprocessor for indicating when said sensed oxygen concentration falls below said minimum selected concentration.

20. The oxygen concentrator of claim 19 including modem means between said microprocessor and said testing apparatus and in communication therewith for receiving quantitative gaseous product flow rate and oxygen concentration signals from said microprocessor and for transmitting said signals to said test apparatus.

21. The oxygen concentrator of claim 20 wherein said modem means comprises a first modem connected to said microprocessor and a second remote modem connected to said test apparatus at a remote location, and wherein said modems are in telephonic communication.

22. The concentrator of claim 21 wherein said microprocessor includes means for signaling said first modem to transmit said signals to said test apparatus when said sensed oxygen concentration falls below said minimum selected concentration.

23. The oxygen concentrator of claim 16 including at least one of the following components:
    (i) first means for sensing peak pressure in said molecular sieve bed, and
    (ii) second means for sensing the line voltage supplied to operate said compressor.

24. The oxgen concentrator of claim 23 wherein said microprocessor cooperates with said first means and said second means and wherein said testing apparatus includes selective digital display means for displaying said peak pressure and said line voltage.

25. The oxygen concentrator of claim 16 wherein said testing apparatus includes means for selecting display of the time required to charge said molecular sieve bed.

26. The oxygen concentrator of claim 16 including a surge tank communicating with said compressor and being charged with air from said compressor when said valve is in an intermediate position between said first and said second positions, and wherein said testing apparatus includes means for selecting display of the time required to charge said surge tank.

* * * * *